United States Patent [19]
McClure et al.

[11] Patent Number: 5,507,732
[45] Date of Patent: Apr. 16, 1996

[54] QUICK ASSEMBLY CATHETER MANIFOLD

[75] Inventors: Robert W. McClure; Ernie P. Gerstmar, both of San Diego; Walter R. Parkola, El Cajon; Matthew S. Gibbons, San Diego; Everett D. Smith, Poway, all of Calif.

[73] Assignee: Medtronic, Inc., Minneapolis, Minn.

[21] Appl. No.: 318,598

[22] Filed: Oct. 5, 1994

[51] Int. Cl.$^6$ .............................. A61M 5/14; A61M 25/00
[52] U.S. Cl. .......................... 604/280; 604/283; 604/256; 604/905
[58] Field of Search ................................. 604/93, 96, 165, 604/167, 264, 272, 275, 278, 280, 283, 284, 905, 256; 606/191, 192, 194

[56] References Cited

U.S. PATENT DOCUMENTS

| | | | |
|---|---|---|---|
| 4,723,550 | 2/1988 | Bales et al. | 604/256 X |
| 4,838,269 | 6/1989 | Robinson . | |
| 4,842,592 | 6/1989 | Caggiani | 604/283 |
| 5,053,015 | 10/1991 | Gross | 604/167 |
| 5,129,887 | 7/1992 | Euteneuer | 606/194 |
| 5,151,087 | 9/1992 | Jonkman | 604/164 |
| 5,203,774 | 4/1993 | Gilson et al. | 604/165 |
| 5,282,790 | 2/1994 | Clement | 604/167 |
| 5,338,313 | 8/1994 | Mollenauer et al. | 604/249 |

*Primary Examiner*—John D. Yasko
*Assistant Examiner*—Adam J. Cermak
*Attorney, Agent, or Firm*—Dianne M. F. Plunkett; Harold R. Patton

[57] ABSTRACT

The present invention is accomplished by providing a catheter manifold (15) having a manifold catheter lumen (115) extending longitudinally therethrough plus a rotationally symmetrical, conically tapering, elastomeric distal seal (65) for gripping the catheter shaft (70), the proximal end of the distal seal (65) having a smaller diameter than the distal end, the distal end of the manifold catheter lumen (115) being conically tapered and sized for a friction fit with the distal seal (65) when the distal seal (65) is inserted into the distal end of the manifold catheter lumen (115), the distal seal (65) having a longitudinally extending distal seal catheter lumen (120). In addition, the catheter manifold (15) has a rotationally symmetrical, conically tapering, elastomeric proximal seal (55) for gripping the guidewire shaft (135), the proximal end of the proximal seal (55) having a larger diameter than the distal end, the proximal end of the manifold catheter lumen (115) having a conical taper sized for a friction fit with the proximal seal (55) when the proximal seal (55) is inserted into the proximal end of the manifold catheter lumen (115), the proximal seal (55) having a longitudinally extending proximal seal catheter lumen (110). The ratio of the proximal seal (55) length to the proximal seal (55) major diameter is about 2 to 1. The ratio of the distal seal (65) length to the distal seal (65) major diameter is about 2 to 1. The ratio of the distal seal (65) minor diameter to the distal seal (65) major diameter is about 1 to 1.5 and the ratio of the proximal seal (55) minor diameter to the proximal seal (55) major diameter is about 1 to 1.5. The proximal (55) and distal seals (65) are made of a 30–50 Shore A USP Class VI elastomer material. In another embodiment, conventional sealing such as threaded parts, adhesive or a Tuohy-Borst connector can be substituted for either of applicant's compression seals.

30 Claims, 3 Drawing Sheets

QUICK ASSEMBLY CATHETER MANIFOLD

FIELD OF THE INVENTION

The present invention relates to catheters, and more particularly, to catheter manifolds.

BACKGROUND OF THE INVENTION

Catheters are tube-like members inserted into the body for diagnostic or therapeutic reasons. One of the therapeutic procedures applicable to the present invention is known as percutaneous transluminal coronary angioplasty (PTCA). This procedure can be used, for example, to reduce arterial build-up of cholesterol fats or atherosclerotic plaque. Typically, a guidewire is threaded through the vascular system to the site of the stenosis and the catheter subsequently tracked over it to the stenosis. The balloon at the distal end of the catheter is then inflated causing the site of the stenosis to widen. After the balloon is deflated, the catheter is withdrawn over the guidewire and another catheter can be slid into place over it if necessary.

Catheters typically have a manifold at their proximal end. The manifold is y-shaped with one arm of the "Y" providing an entrance port for the guidewire and the other arm of the "Y" providing an entrance port for inflation liquids. The manifold typically interconnects with a Luer coupler on its proximal end. The Luer coupler provides a guidewire entry port and interfaces with the manifold's straight arm which receives the guidewire. Manifolds typically have one or more seals to provide the sealing necessary to hold pressure under balloon inflation and maintain vacuum under balloon deflation.

Prior art manifold designs use threaded parts or adhesives to structurally join components. With adhesively bonded seals, bonding dissimilar materials presents difficulties. Prior art designs using threaded parts or adhesively bonded parts must have tightly controlled, highly accurate molded parts. Such parts are expensive to manufacture. What is needed is a seal which will eliminate the need for such tight tolerances, thereby reducing manufacturing time and expense.

Catheters are typically used in darkened environments to permit the physician to use fluoroscopy to monitor the movement of the balloon through the vascular system, the balloon having a radiopaque marker band. What is needed is a manifold which will be visible to the physician in a darkened laboratory during the PTCA procedure.

U.S. Pat. No. 5,129,887 to Euteneuer et al. for "Adjustable Manifold for Dilatation Catheter" discloses a threaded means 50/52, 125/126 and 160/170 for compressing seals 70, 134 and 168 in FIGS. 5, 6 and 7 respectively. For example, compression seal 70 is described at col. 5, lines 22–28 as being "a generally cylindrical resilient member having an outside diameter to fit within the wide interior passage 54B of cap 28, and having a central aperture 72 sized to receive outer tubing 14, which extends therethrough. One end of seal 70 abuts against distal end 30 of the inflation manifold 24, and the other end engages flange 66A of strain relief 66 against the flat side of washer 68". When cap 28 is screwed more tightly onto inflation manifold 24, this causes pressure on compression seal 70 which deforms (radially inwardly) to press outer member 14 against hypotube 64 with sufficient pressure that it is effectively locked in place by frictional forces. See col. 5, lines 32–37.

U.S. Pat. No. 4,838,269 to Robinson et al. for "Manifold for Angioplasty Balloon Catheter" discloses a threaded means of compressing a seal. "By rotation of the valve nut 110, sealing or unsealing of the compression or wire sealing O-ring 270 against a guide wire may be achieved". See col. 5, lines 38–40.

U.S. Pat. No. 4,842,592 to Caggiani et al. for "Connector Assembly" discloses a compression plug 6 within cavity 35, which compression causes constriction of the channel 38 and thereby secures the catheter 1 within the connector assembly 3. See col. 6, lines 47–50.

U.S. Pat. No. 5,203,774 to Gilson et al. for "Device for use with a Catheter" discloses a Touhy-Borst connector which "closes onto the external diameter of a sleeve, thus creating a seal between the Tuohy-Borst connector without impairing freedom of movement of the catheter within the sleeve". See col. 1, lines 59–62.

An object of the present invention is to provide a manifold which eliminates the need for adhesive seals and threaded parts with tight tolerances on molded parts. Another object of the invention is to provide a manifold which is visible in a darkened laboratory.

SUMMARY OF THE INVENTION

The above features and advantages of the present invention, as well as others, are accomplished by providing a catheter manifold having a manifold catheter lumen extending longitudinally therethrough plus a rotationally symmetrical, conically tapering, elastomeric distal seal for gripping the catheter shaft, the proximal end of the distal seal having a smaller diameter than the distal end, the distal end of the manifold catheter lumen being conically tapered and sized for a friction fit with the distal seal when the distal seal is inserted into the distal end of the manifold catheter lumen, the distal seal having a longitudinally extending distal seal catheter lumen. In addition the catheter manifold has a rotationally symmetrical, conically tapering, elastomeric proximal seal for gripping the guidewire shaft, the proximal end of the proximal seal having a larger diameter than the distal end, the proximal end of the manifold catheter lumen having a conical taper sized for a friction fit with the proximal seal when the proximal seal is inserted into the proximal end of the manifold catheter lumen, the proximal seal having a longitudinally extending proximal seal catheter lumen. The ratio of the proximal seal length to the proximal seal major diameter is about 2 to 1 and the ratio of the distal seal length to the distal seal major diameter is about 2 to 1. The ratio of the distal seal minor diameter to the distal seal major diameter is about 1 to 1.5 and the ratio of the proximal seal minor diameter to the proximal seal major diameter is about 1 to 1.5. The proximal and distal seals are made of a 30–50 Shore A USP Class VI elastomer material. In another embodiment, any conventional means for sealing such as threaded parts, adhesive or a Tuohy-Borst connector can be substituted for either of applicant's compression seals.

DETAILED DESCRIPTION OF THE PREFERRED EMBODIMENTS

Figure 1:
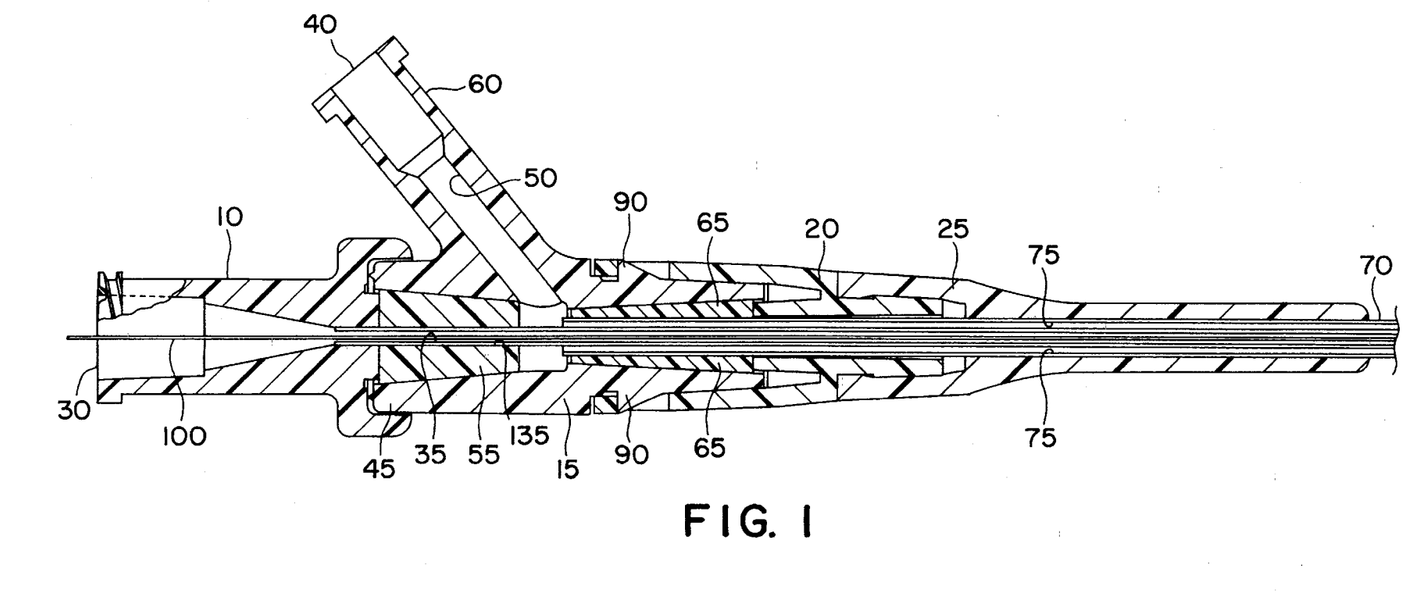
FIG. 1 is a longitudinal cross-section of the present invention with all major components integrated.

Referring to FIG. 1, adhesive seals and threaded parts have been eliminated by using ultrasonically welded and snap fit components to capture two compression seals 55 and 65 against the molded plastic surfaces. The seal against both the catheter shaft 70 and the guidewire shaft 135 is produced by mechanically expanding two compression seals respectively the distal seal 65 and the proximal seal 55, and allowing them to grip the outer diameter when the expander is removed. Although applicant's invention is illustrated with two compression seals, one skilled in the art would recognize that either seal could be replaced with a conventional method of sealing such as threaded parts, adhesive, or a Tuohy-Borst adapter. The manifold 15 of the present invention is visible in a darkened laboratory because the retainer cap 20 has been impregnated with phosphorescent pigment.

Conventional catheter manifolds with threaded parts and adhesive seals require molding tolerances on the order of plus or minus 0.0127 mm (plus or minus 0.0005 inches). Using applicant's design, molding tolerances can be increased to plus or minus 0.127 mm (plus or minus 0.005 inches). Tighter tolerances mean more expensive tools, higher reject rates and lower yields. In general, every 1% increase in catheter tolerances results in a 10% decrease in costs.

Ultrasonic welding of thermoplastic parts is accomplished by using a metallic horn to apply high frequency vibrations to the pieces being assembled. The vibrations, through applied force as well as surface and intermolecular friction produce a sharp rise in temperature at the joint. When the temperature is high enough to melt the plastic, there is a "flow" of material between the parts. When the vibrations stop, the material solidifies under pressure and a uniform weld results. Most plastic welders operate above the range of human hearing at 20,000 Hertz (20 Khz) and thus are called "ultrasonic". A power supply supplies high frequency electrical energy to the converter which changes this energy to mechanical or vibratory energy. Coupled to the converter is a booster which determines the amplitude of vibration produced at the face of the horn. The purpose of the horn is to transfer the ultrasonic vibrations from the converter to the parts to be welded and to apply the necessary pressure to achieve a weld. The converter-booster-horn assembly is lowered and raised over the workpiece by a pneumatic system, which brings the horn in contact with the part at a predetermined pressure and velocity. Ultrasonic welding can be accomplished with a Branson 900 series computer controlled welder, for example.

Figure 2:
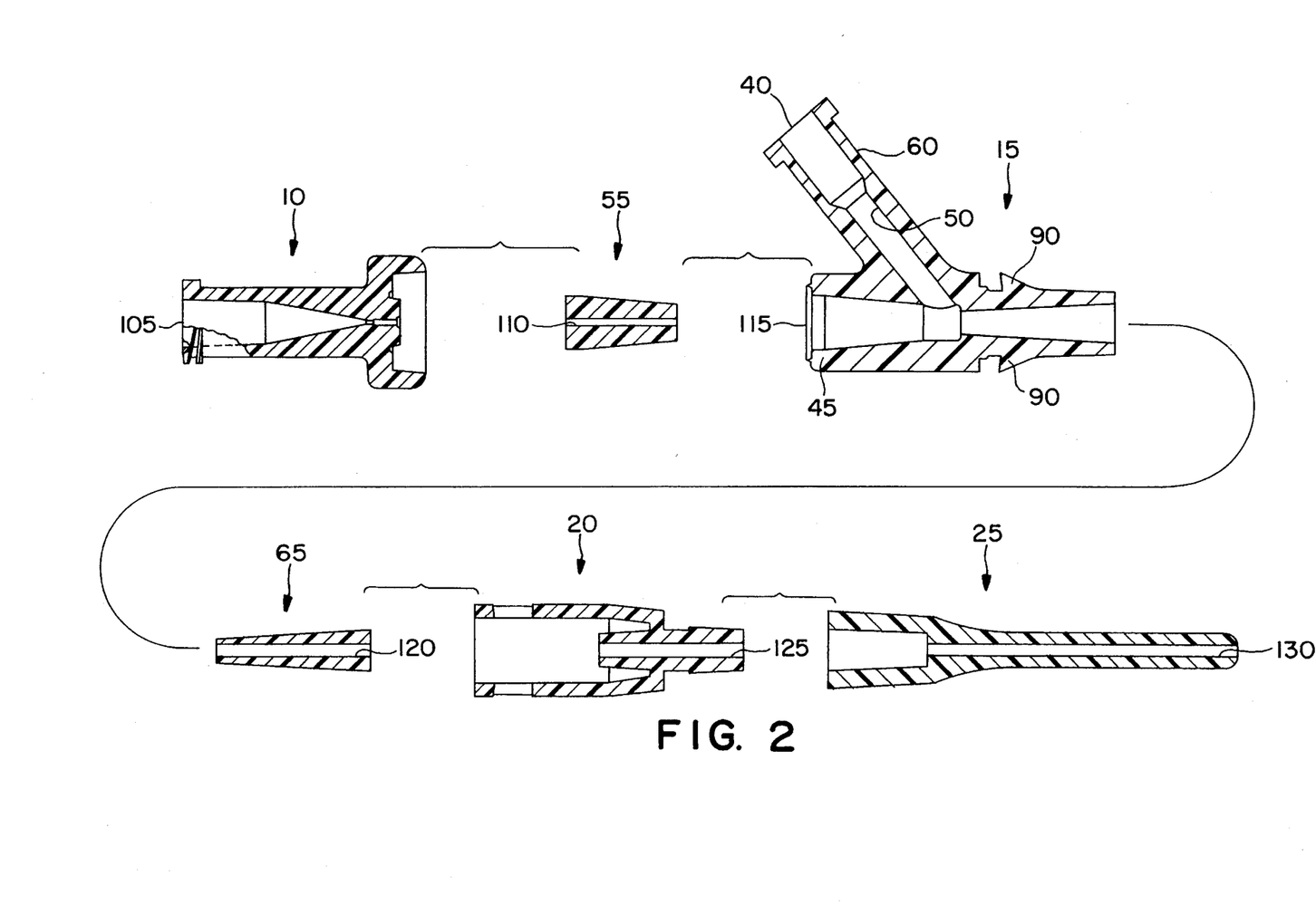
FIG. 2 is a longitudinal cross-section of the present invention with the major components in assembly sequence.

FIG. 1 represents a longitudinal cross-section of the present invention with all major components integrated. FIG. 2 represents the same set of components in assembly sequence. These components are the Luer coupler 10, the proximal seal 55, the manifold 15, the distal seal 65, the retainer cap 20 and the strain relief 25. The catheter shaft 70 passes through six pieces, the Luer coupler catheter lumen 105, the proximal seal catheter lumen 110, the manifold catheter lumen 115, the distal seal catheter lumen 120, the retainer cap catheter lumen 125 and the strain relief catheter lumen 130.

The purpose of the rotationally symmetrical Luer coupler 10 is to provide an entry port 30 for a guidewire as well as to support the guidewire lumen 35. The Luer coupler 10 is of conventional design having a guidewire port 30 at its proximal end. A guidewire shaft 135 defining a guidewire lumen 35 extends longitudinally through the Luer coupler catheter lumen 105, the proximal seal catheter lumen 110 and the catheter shaft 70. The catheter shaft 70 extends longitudinally through the distal seal 65, the retainer cap 20 and the strain relief catheter lumen 75. The Luer coupler 10 can be made of a modified styrene or a polycarbonate. A modified styrene is preferred because it is clear, enabling the physician to view liquids during purging to ascertain whether injurious air bubbles have been eliminated. Furthermore, modified styrenes retain their clarity and do not yellow during radiation sterilization as do polycarbonates.

Figure 3:
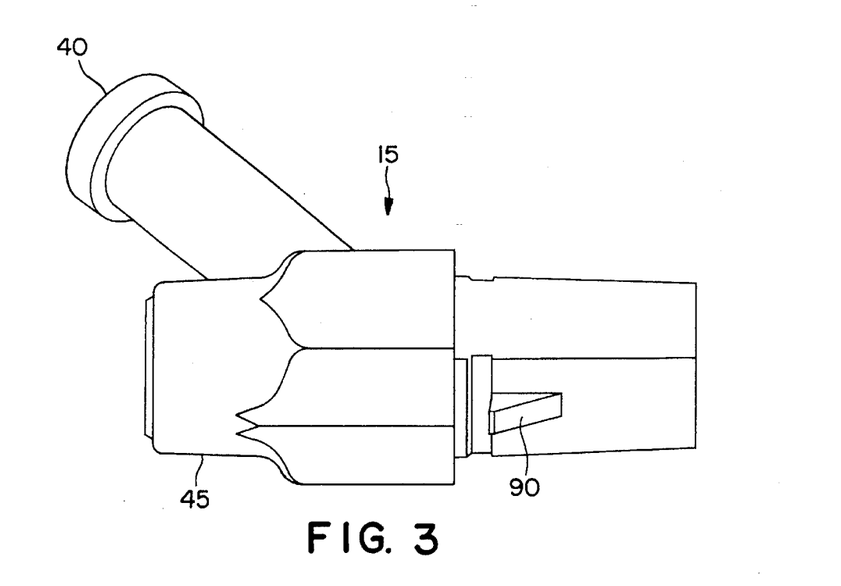
FIG. 3 is a perspective view of the manifold 15.

The purpose of the manifold 15 is to provide an inflation port 40, a guidewire lumen 35, inflation lumen 50 and the sealing required to hold pressure under balloon inflation as well as vacuum under balloon deflation. The manifold 15 has a first arm 60 which accommodates the inflation port 40 and manifold inflation lumen 50 which is in fluid communication with the catheter inflation lumen 75. A second arm 45 accommodates the guidewire lumen 35. To accomplish sealing, the manifold 15 has a rotationally symmetrical proximal seal 55 within the proximal end of the manifold catheter lumen 115 and a rotationally symmetrical distal seal 65 in the distal end of the manifold catheter lumen 115. The seals 55 and 65 are made of a low durometer material, as for example, a 30–50 Shore A USP Class VI elastomer designed to conform to the inner shape of the manifold 15 barrel both under pressure and under vacuum. The distal end of the Luer coupler 10 is sized to fit over the proximal end of the second arm 45 of the manifold 15.

The Luer coupler 10 is ultrasonically welded onto the manifold 15, capturing and compressing the conically shaped, rotationally symmetrical proximal seal 55. The inner diameter of the proximal seal catheter lumen 110 will vary with the size catheter to be passed therethrough. The proximal seal 55 outer diameter is sized for a compression fit within the manifold catheter lumen 115. It is important that the following dimensional relationships be observed when designing a proximal seal 55. The ratio of the proximal seal 55 length to the proximal seal 55 major diameter (found at the proximal seal 55 proximal end) is preferably 2 to 1. The ratio of the proximal seal 55 minor diameter (found at the proximal seal 55 distal end) to the proximal seal major diameter is preferably 1 to 1.5. If the proximal seal 55 is too long in proportion to the major diameter, the proximal seal 55 will ripple and not provide a proper seal and mechanical retention of the guidewire shaft 135. With the preferred ratios, the elastomer proximal seal 55 will fill all available space when compression is applied.

A snap fit retainer cap 20 is used to maintain the rotationally symmetrical distal seal 65 in place. The retainer cap 20 applies compressive force to the seal and grips the catheter shaft 70. The inner diameter of the distal seal catheter lumen 120 will vary with the size catheter to be passed therethrough. The outer diameter of the distal seal 65 is sized for a compression fit within the retainer cap catheter lumen 125. It is important that the following dimensional relationships be observed when designing a distal seal 65. The ratio of the distal seal 65 length to the distal seal 65 major diameter (found at the distal seal 65 distal end) is preferably 2 to 1. The ratio of the distal seal 65 minor diameter (found at the distal seal 65 proximal end) to the distal seal 65 major diameter is preferably 1 to 1.5. If the distal seal 65 is too long in proportion to the major diameter, the distal seal 65 will ripple and not provide a proper seal and mechanical retention of the catheter shaft 70. With the preferred ratios, the elastomer distal seal 65 will fill all available space when compression is applied.

Applicant's proximal seal 55 and distal seal 65 are preferable to the conventional Tuohy-Borst connector which has two pieces which screw together around the catheter causing the Tuohy-Borst Connector material to wrinkle and collapse under the compression fit of the Tuohy-Borst connector. Applicant's elastomer seal provides uniform sealing between the proximal seal 55 inner diameter and the guidewire shaft 135 outer diameter. The distal seal 65 provides a uniform sealing between the distal seal 65 inner diameter and the catheter shaft 70 outer diameter.

Figure 4:
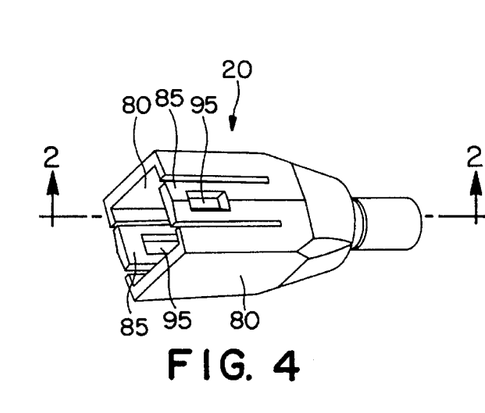
FIG. 4 is a side perspective view of the retainer cap 20 which is shown in cross-section in FIG. 2.
Figure 5:
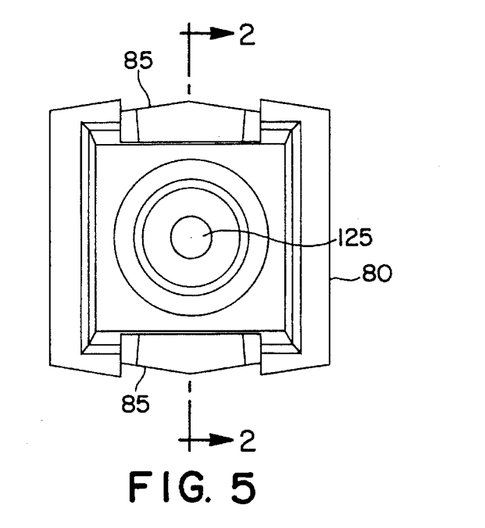
FIG. 5 is a plan view of the proximal end of the retainer cap 20 which is shown in cross-section in FIG. 2.

The retainer cap 20 can be made of a modified styrene or a polycarbonate. The retainer cap 20 is a distally tapering square shape with two opposing flat sides 80 for ease in gripping, and two opposing tabs 85 at a right angle to the flat sides 80, each tab 85 with two slots 95 aligned to engage complimentary hooks 90 on the manifold 15. Once the retainer cap 20 is snapped in place, it cannot be removed without breaking the tabs. This insures that it will not disengage while in the patient. The retainer cap 20 is impregnated with phosphorescent pigment so that it can be readily found in the darkened catheter laboratory. Although other components at the distal end of the catheter could be impregnated with phosphorescent pigment, the retainer cap 20 is especially desirable for the impregnation because it need not be clear since it is not used in the purging process and bubbles need not be viewed through it.

The purpose of the strain relief 25 is to reduce kinking as the catheter shaft 70 bends. The strain relief 25 can be made of a low durometer material such as a 30–50 Shore A USP class VI elastomer. The strain relief is molded such that its proximal end forms a compression fit with the distal end of the retainer cap 20.

The assembly process is as follows. The strain relief 25 is loaded over the proximal end of the catheter shaft 70 followed by the retainer cap 20 being loaded over the proximal end of the catheter shaft 70. The distal seal 65 is expanded with a hypotube which is placed within the distal seal catheter lumen 120, then the distal seal 65 is slid over the proximal end of the catheter shaft 70. The proximal end of the catheter shaft 70 is then loaded into the distal end of the manifold 15. Next, the retainer cap 20 is seated, proximal end first, into the distal end of the manifold 15 followed by the strain relief 25 being seated over the retainer cap 20. The proximal seal 55 is expanded with a hypotube which is placed within the proximal seal catheter lumen 110. The proximal seal 55 is then slid within the manifold catheter lumen 115 and over the guidewire shaft 135. The proximal seal 55 is subsequently seated in the proximal end of the manifold 15. Finally, the distal end of the Luer coupler 10 is then placed over the proximal end of the manifold 15 and sonically welded in place.

The manifold 15 will no longer need tight molding tolerances because the conically shaped proximal 55 and distal 65 seals designed into this assembly will allow all spaces to be filled and sealed with surface to surface contact by mere compression of the elastomer. Pressure and vacuum sealing is accomplished regardless of how the rest of the assembly is held together, i.e., by ultrasonic welding, snap in place parts, etc. The elastomer proximal 55 and distal 65 seal design can be adapted to any catheter shaft 70 sizes provided that the proximal 55 and distal 65 seal ratios supra are observed. With ultrasonically welded and snap fit parts, viscous adhesives have been eliminated. Problems stemming from trying to bond to materials such as polyethylene and polypropylene which have low surface tensions have been eliminated through the use of the proximal seal 55 and distal seal 65.

Process time for building manifolds using ultrasonic welding is less than the process time for parts using adhesives because the curing time for conventional adhesives has been eliminated entirely. Additionally, environmental concerns over the release of hazardous fumes from the adhesive have been eliminated.

The preceding specific embodiments are illustrative of the practice of the invention. It is to be understood, however, that other expedients known to those skilled in the art or disclosed herein, may be employed without departing from the spirit of the invention or the scope of the appended claims.

| No. | Component |
|-----|-----------|
| 10  | Luer Coupler |
| 15  | Manifold |
| 20  | Retainer Cap |
| 25  | Strain Relief |
| 30  | Guidewire Port |
| 35  | Guidewire Lumen |
| 40  | Inflation Port |
| 45  | Second Arm |
| 50  | Manifold Inflation Lumen |
| 55  | Proximal Seal |
| 60  | First Arm |
| 65  | Distal Seal |
| 70  | Catheter Shaft |
| 75  | Catheter Inflation Lumen |
| 80  | Flat Sides |
| 85  | Tabs |
| 90  | Hook |
| 95  | Slots |
| 100 | Guidewire |
| 105 | Luer Coupler Catheter Lumen |
| 110 | Proximal Seal Catheter Lumen |
| 115 | Manifold Catheter Lumen |
| 120 | Distal Seal Catheter Lumen |
| 125 | Retainer Cap Catheter Lumen |
| 130 | Strain Relief Catheter Lumen |
| 135 | Guidewire Shaft |

What is claimed is:

1. A catheter manifold comprising:

a manifold having a proximal end, a distal end and a manifold catheter lumen extending longitudinally therethrough;

a rotationally symmetrical, conically tapering, elastomeric distal seal having a distal end and a proximal end, the proximal end having a smaller diameter than the distal end, the distal seal proximal end diameter defining a minor diameter, the distal seal distal end defining a major diameter, the distal end of the manifold catheter lumen being conically tapered and forming a friction fit with the distal seal, the distal seal being inserted into the distal end of the manifold catheter lumen, the distal seal having a longitudinally extending distal seal catheter lumen; and a rotationally symmetrical, conically tapering, elastomeric proximal seal having a distal end and a proximal end, the proximal end having a larger diameter than the distal end, the proximal end diameter defining a major diameter, the distal end diameter defining a minor diameter, the proximal end of the manifold catheter lumen having a conical taper forming a friction fit with the proximal seal, the proximal seal being inserted into the proximal end of the manifold catheter lumen, the proximal seal having a longitudinally extending proximal seal catheter lumen.

2. A catheter manifold according to claim 1 further comprising:
   a catheter shaft having an outer diameter and the catheter shaft defining a catheter inflation lumen, the catheter shaft extending longitudinally through the distal seal catheter lumen, the distal seal sealingly gripping the outer diameter of the catheter shaft; and
   a guidewire shaft defining a guidewire lumen, the guidewire shaft extending longitudinally through the proximal seal catheter lumen, the manifold catheter lumen and the catheter inflation lumen, the proximal seal sealingly gripping the outer diameter of the guidewire shaft.

3. A catheter manifold according to claim 1 wherein the ratio of the proximal seal length to the proximal seal major diameter is about 2 to 1 and wherein the ratio of the distal seal length to the distal seal major diameter is about 2 to 1.

4. A catheter manifold according to claim 1 wherein the ratio of the distal seal minor diameter to the distal seal major diameter is about 1 to 1.5 and the ratio of the proximal seal minor diameter to the proximal seal major diameter is about 1 to 1.5.

5. A catheter manifold according to claim 1 wherein the proximal and distal seals are made of a 30–50 Shore A USP Class VI elastomer material.

6. A catheter manifold according to claim 1 further comprising a Luer coupler having a proximal end, a distal end, a Luer coupler catheter lumen extending longitudinally therethrough, the Luer coupler having a distal end fitting over the proximal end of the manifold.

7. A catheter manifold according to claim 6 wherein the distal end of the Luer Coupler is ultrasonically welded to the proximal end of the manifold.

8. A catheter manifold according to claim 1 further comprising:
   two opposing hooks proximal to the distal end of the manifold; and
   a retainer cap having a longitudinally extending retainer cap catheter lumen extending therethrough, the retainer cap tapering distally and having two first opposing flat sides and two second opposing flat sides at right angles to the two first opposing flat sides, each second opposing side having a tab with a slot aligned to engage the complimentary hooks on the manifold, the proximal end of the retainer cap fitting over the distal end of the manifold.

9. A catheter manifold according to claim 8 further comprising the retainer cap, such that the retainer cap cannot be removed from the manifold without breaking the tabs.

10. A catheter manifold according to claim 8 wherein the retainer cap has been impregnated with phosphorescent pigment.

11. A catheter manifold comprising:
    a manifold having a proximal end, a distal end and a manifold catheter lumen extending longitudinally therethrough;
    a rotationally symmetrical, conically tapering, elastomeric distal seal having a distal end and a proximal end, the proximal end having a smaller diameter than the distal end, the distal seal proximal end diameter defining a minor diameter, the distal seal distal end defining a major diameter, the distal end of the manifold catheter lumen being conically tapered forming a friction fit with the distal seal, the distal seal being inserted into the distal end of the manifold catheter lumen, the distal seal having a longitudinally extending distal seal catheter lumen, wherein the ratio of the distal seal length to the distal seal major diameter is about 2 to 1, and wherein the ratio of the distal seal minor diameter to the distal seal major diameter is about 1 to 1.5;
    a rotationally symmetrical, conically tapering, elastomeric proximal seal having a distal end and a proximal end, the proximal end having a larger diameter than the distal end, the proximal end diameter defining a major diameter, the distal end diameter defining a minor diameter, the proximal end of the manifold catheter lumen having a conical taper forming a friction fit with the proximal seal, the proximal seal being inserted into the proximal end of the manifold catheter lumen, the proximal seal having a longitudinally extending proximal seal catheter lumen, wherein ratio of the proximal seal length to the proximal seal major diameter is about 2 to 1 and wherein the ratio of the proximal seal minor diameter to the proximal seal major diameter is about 1 to 1.5;
    a catheter shaft having an outer diameter and the catheter shaft defining a catheter inflation lumen, the catheter shaft extending longitudinally through the distal seal catheter lumen, the distal seal sealingly gripping the outer diameter of the catheter shaft; and
    a guidewire shaft defining a guidewire lumen, the guidewire shaft extending longitudinally through the proximal seal catheter lumen, the manifold catheter lumen and the catheter inflation lumen, the proximal seal sealingly gripping the outer diameter of the guidewire shaft.

12. A catheter manifold according to claim 11 wherein the proximal and distal seals are made of a 30–50 Shore A USP Class VI elastomer material.

13. A catheter manifold comprising:
    a manifold having a proximal end, a distal end and a manifold catheter lumen extending longitudinally therethrough;
    a rotationally symmetrical, conically tapering, elastomeric distal seal having a distal end and a proximal end, the proximal end having a smaller diameter than the distal end, the distal seal proximal end diameter defining a minor diameter, the distal seal distal end defining a major diameter, the distal end of the manifold catheter lumen being conically tapered and forming a friction fit with the distal seal, the distal seal being inserted into the distal end of the manifold catheter lumen, the distal seal having a longitudinally extending distal seal catheter lumen;
    a catheter shaft having an outer diameter and the catheter shaft defining a catheter inflation lumen, the catheter shaft extending longitudinally through the distal seal catheter lumen, the distal seal sealingly gripping the outer diameter of the catheter shaft;
    a guidewire shaft defining a guidewire lumen, the guidewire shaft extending longitudinally through the manifold catheter lumen and the catheter inflation lumen; and
    a means for sealingly gripping the outer diameter of the guidewire shaft.

14. A catheter manifold according to claim 13 wherein the ratio of the distal seal length to the distal seal major diameter is about 2 to 1, and wherein the ratio of the distal seal minor diameter to the distal seal major diameter is about 1 to 1.5.

15. A catheter manifold according to claim 13 wherein the distal seal is made of a 30–50 Shore A USP Class VI elastomer material.

16. A catheter manifold according to claim 13 further comprising a Luer coupler having a proximal end, a distal end, a Luer coupler catheter lumen extending longitudinally therethrough, the Luer coupler having a distal end fitting over the proximal end of the manifold.

17. A catheter manifold according to claim 16 wherein the distal end of the Luer Coupler is ultrasonically welded to the proximal end of the manifold.

18. A catheter manifold according to claim 13 further comprising:

two opposing hooks proximal to the distal end of the manifold; and a retainer cap having a longitudinally extending retainer cap catheter lumen extending therethrough, the retainer cap tapering distally and having two first opposing flat sides and two second opposing flat sides at right angles to the two first opposing flat sides, each second opposing side having a tab with a slot aligned to engage complimentary hooks on the manifold, the proximal end of the retainer cap fitting over the distal end of the manifold.

19. A catheter manifold according to claim 18 further comprising the retainer cap, such that the retainer cap cannot be removed from the manifold without breaking the tabs.

20. A catheter manifold according to claim 19 wherein the retainer cap is impregnated with phosphorescent pigment.

21. A catheter manifold comprising:

a manifold having a proximal end, a distal end and a manifold catheter lumen extending longitudinally therethrough;

a rotationally symmetrical, conically tapering, elastomeric proximal seal having a distal end and a proximal end, the proximal end having a larger diameter than the distal end, the proximal end diameter defining a major diameter, the distal end diameter defining a minor diameter, the proximal end of the manifold catheter lumen having a conical taper having a friction fit with the proximal seal, the proximal seal being inserted into the proximal end of the manifold catheter lumen, the proximal seal having a longitudinally extending proximal seal catheter lumen;

a catheter shaft having an outer diameter and the catheter shaft; defining a catheter inflation lumen, the catheter shaft extending longitudinally through the manifold catheter lumen;

a means for sealingly gripping the outer diameter of the catheter shaft; and a guidewire shaft defining a guidewire lumen, the guidewire shaft extending longitudinally through the proximal seal catheter lumen, the manifold catheter lumen and the catheter inflation lumen, the proximal seal sealingly gripping the outer diameter of the guidewire shaft.

22. A catheter manifold according to claim 21 wherein ratio of the proximal seal length to the proximal seal major diameter is about 2 to 1 and wherein the ratio of the proximal seal minor diameter to the proximal seal major diameter is about 1 to 1.5.

23. A catheter manifold according to claim 21 wherein proximal seal is made of a 30–50 Shore A USP Class VI elastomer material.

24. A catheter manifold according to claim 21 further comprising a Luer coupler having a proximal end, a distal end, a Luer coupler catheter lumen extending longitudinally therethrough, the Luer coupler having a distal end fitting over the proximal end of the manifold.

25. A catheter manifold according to claim 24 wherein the distal end of the Luer Coupler is ultrasonically welded to the proximal end of the manifold.

26. A catheter manifold according to claim 21 further comprising:

two opposing hooks proximal to the distal end of the manifold; and a retainer cap having a longitudinally extending retainer cap catheter lumen extending therethrough, the retainer cap tapering distally and having two first opposing flat sides and two second opposing flat sides at right angles to the two first opposing flat sides, each second opposing side having a tab with a slot aligned to engage complimentary hooks on the manifold, the proximal end of the retainer cap fitting over the distal end of the manifold.

27. A catheter manifold according to claim 26 further comprising the retainer cap, such that the retainer cap cannot be removed from the manifold without breaking the tabs.

28. A catheter manifold according to claim 27 wherein the retainer cap is impregnated with phosphorescent pigment.

29. A method of catheter manifold assembly comprising the steps of: Providing a manifold comprising;

the manifold having a proximal end, a distal end and a manifold catheter lumen extending longitudinally therethrough;

a rotationally symmetrical, conically tapering, elastomeric distal seal having a distal end and a proximal end, the proximal end having a smaller diameter than the distal end, the distal seal proximal end diameter defining a minor diameter, the distal seal distal end defining a major diameter, the distal end of the manifold catheter lumen being conically tapered and forming a friction fit with the distal seal, the distal seal being inserted into the distal end of the manifold catheter lumen, the distal seal having a longitudinally extending distal seal catheter lumen;

a rotationally symmetrical, conically tapering, elastomeric proximal seal having a distal end and a proximal end, the proximal end having a larger diameter than the distal end, the proximal end diameter defining a major diameter, the distal end diameter defining a minor diameter, the proximal end of the manifold catheter lumen having a conical taper forming a friction fit with the proximal seal, the proximal seal being inserted into the proximal end of the manifold catheter lumen, the proximal seal having a longitudinally extending proximal seal catheter lumen; and two opposing hooks proximal to the distal end of the manifold: providing a catheter shaft; providing a retainer cap comprising:

the retainer cap having a longitudinally extending retainer cap catheter lumen extending therethrough, the retainer cap tapering distally and having two first opposing flat sides and two second opposing flat sides at right angles to the two first opposing flat sides, each second opposing side having a tab with a slot aligned to engage the complimentary hooks on the manifold, the proximal end of the retainer cap fitting over the distal end of the manifold; providing a Luer coupler comprising:

a proximal end, a distal end, a Luer coupler catheter lumen extending longitudinally therethrough, the Luer coupler having a digital end fitting over the proximal end of the manifold;

loading the retainer cap over the proximal end of the catheter shaft;

expanding the distal seal by placing a hypotube in the distal seal catheter lumen;

sliding the distal seal over the proximal end of the catheter shaft;

loading the proximal end of the catheter shaft into the distal end of the manifold;

seating the retainer cap proximal end into the distal end of the manifold;

expanding the proximal seal with a hypotube within the proximal seal catheter lumen;

loading the proximal seal into the proximal end of the manifold;

placing the distal end of the Luer coupler over the proximal end of the manifold; and ultrasonically welding the Luer coupler to the manifold.

30. A method of catheter manifold assembly comprising the steps of:

providing a manifold having a manifold catheter lumen extending longitudinally therethrough;

providing a distal seal having a longitudinally extending distal seal catheter lumen;

providing a proximal seal having a longitudinally extending proximal seal catheter lumen;

providing a catheter shaft;

providing a retainer cap having a longitudinally extending retainer cap catheter lumen;

providing a Luer coupler having a longitudinally extending Luer coupler catheter lumen;

sliding the catheter shaft into the retainer cap catheter lumen;

sliding the distal seal over the catheter shaft proximal to the retainer cap;

loading the proximal end of the catheter shaft into the distal end of the manifold;

seating the retainer cap proximal end into the distal end of the manifold;

loading the proximal seal into the proximal end of the manifold;

placing the distal end of the Luer coupler over the proximal end of the manifold; and ultrasonically welding the Luer coupler to the manifold.

* * * * *

UNITED STATES PATENT AND TRADEMARK OFFICE
CERTIFICATE OF CORRECTION

PATENT NO. : 5,507,732
DATED : April 16, 1996
INVENTOR(S) : McClure et al.

It is certified that error appears in the above-indentified patent and that said Letters Patent is hereby corrected as shown below:

Column 9, Line 44, "shaft;" should be --shaft--.

Column 10, Line 64, "digital" should be --distal--.

Signed and Sealed this

Thirteenth Day of May, 1997

Attest:

BRUCE LEHMAN

Attesting Officer

Commissioner of Patents and Trademarks